US006578348B1

(12) United States Patent  (10) Patent No.: US 6,578,348 B1
Banks  (45) Date of Patent: Jun. 17, 2003

(54) METHOD AND PACKAGING SYSTEM FOR PACKAGING A STERILIZED ITEM

(76) Inventor: Percival C. Banks, 1301 Quarry Ct., Ste. 204, Pt. Richmond, CA (US) 94801

( * ) Notice: Subject to any disclaimer, the term of this patent is extended or adjusted under 35 U.S.C. 154(b) by 0 days.

(21) Appl. No.: 09/616,100

(22) Filed: Jul. 14, 2000

(51) Int. Cl.⁷ .............................................. B65B 55/02
(52) U.S. Cl. .............................. 53/425; 53/459; 53/570
(58) Field of Search ........................... 53/133.1, 133.3, 53/411, 425, 459, 464, 469, 570; 206/439, 459.5; 220/495.11; 383/88, 127

(56) References Cited

U.S. PATENT DOCUMENTS

| 2,023,782 A | * | 12/1935 | Driver .......................... 229/76 |
| 2,915,173 A | * | 12/1959 | Langdon ........................ 206/7 |
| 3,446,420 A | * | 5/1969 | Rinecker ...................... 229/62 |
| 3,494,726 A | * | 2/1970 | Barasch ........................ 422/29 |
| 3,680,772 A | * | 8/1972 | Hoover ......................... 229/79 |
| 3,991,881 A | * | 11/1976 | Augurt ......................... 206/439 |
| 4,177,620 A | * | 12/1979 | Daly et al. ..................... 53/425 |
| 4,350,246 A | * | 9/1982 | Mayer .......................... 206/210 |
| 4,506,787 A | * | 3/1985 | Bruso .......................... 206/363 |
| 4,705,171 A | * | 11/1987 | Eldridge ....................... 206/438 |
| 4,852,783 A | * | 8/1989 | Bryden et al. ................. 224/253 |
| 4,962,856 A | * | 10/1990 | Carter ......................... 206/439 |
| 5,638,661 A | * | 6/1997 | Banks .......................... 53/469 |

* cited by examiner

Primary Examiner—Scott A. Smith
Assistant Examiner—Nathaniel Chukwurah
(74) Attorney, Agent, or Firm—H. Michael Brucker

(57) ABSTRACT

A method, packaging system and packaging element for packaging a sterilizable item for aseptic presentation onto a sterile field wherein the vertical orientation of the sterilizable item does not need to be reversed during packaging, sterilization, unpackaging or presentation and instructions for handling are printed on the packaging element so that they are exposed when the packaging element is folded according to the packaging system and method.

8 Claims, 5 Drawing Sheets

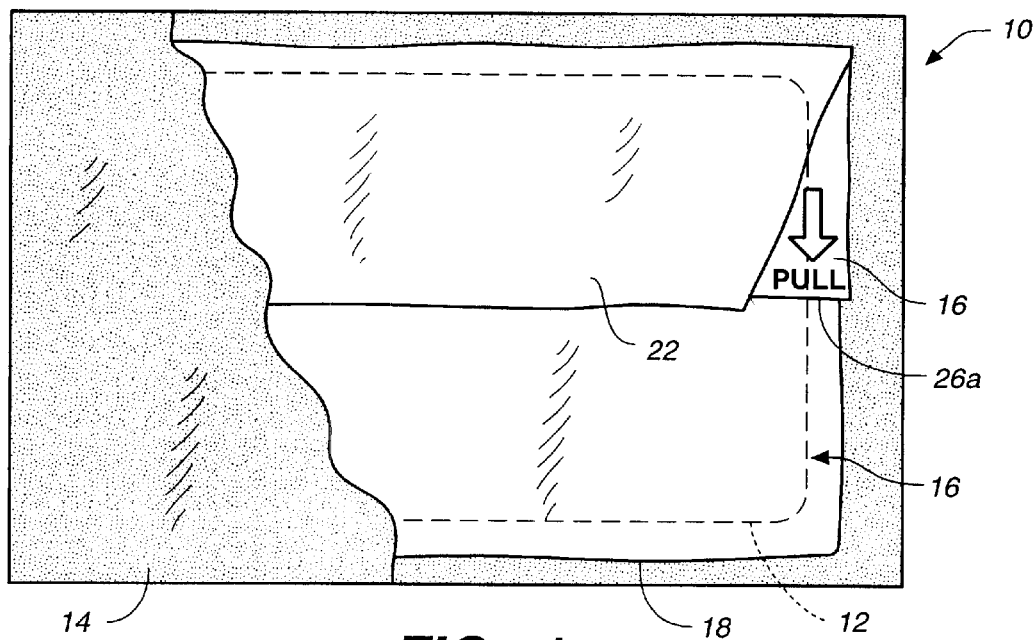
FIG._1
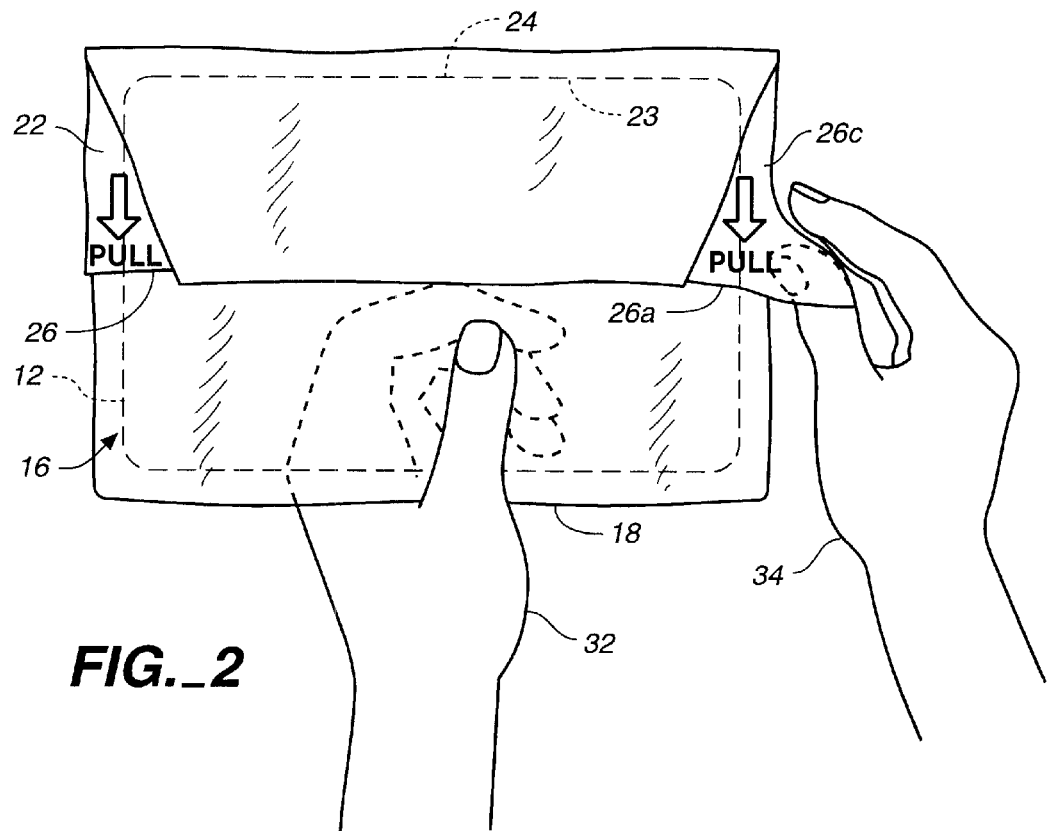
FIG._2

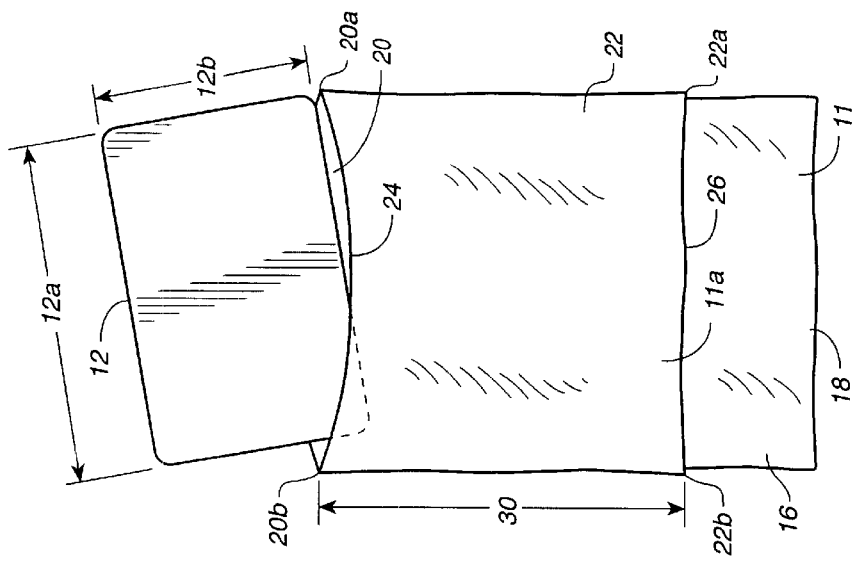
FIG._4
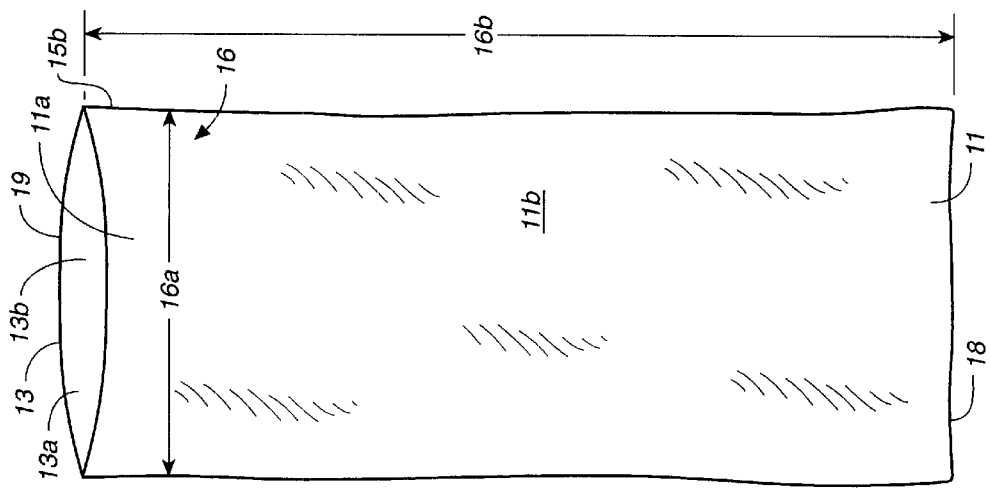
FIG._3

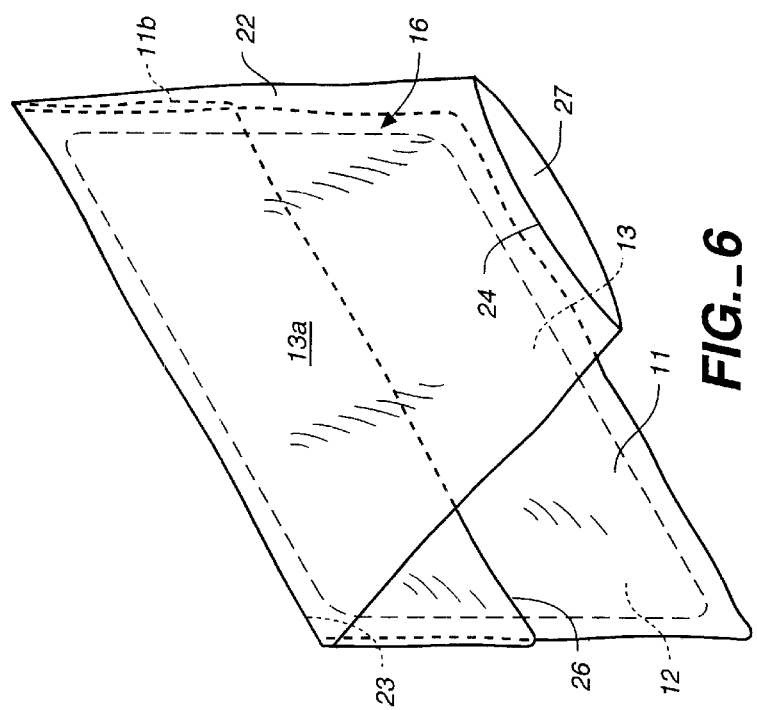
FIG._6
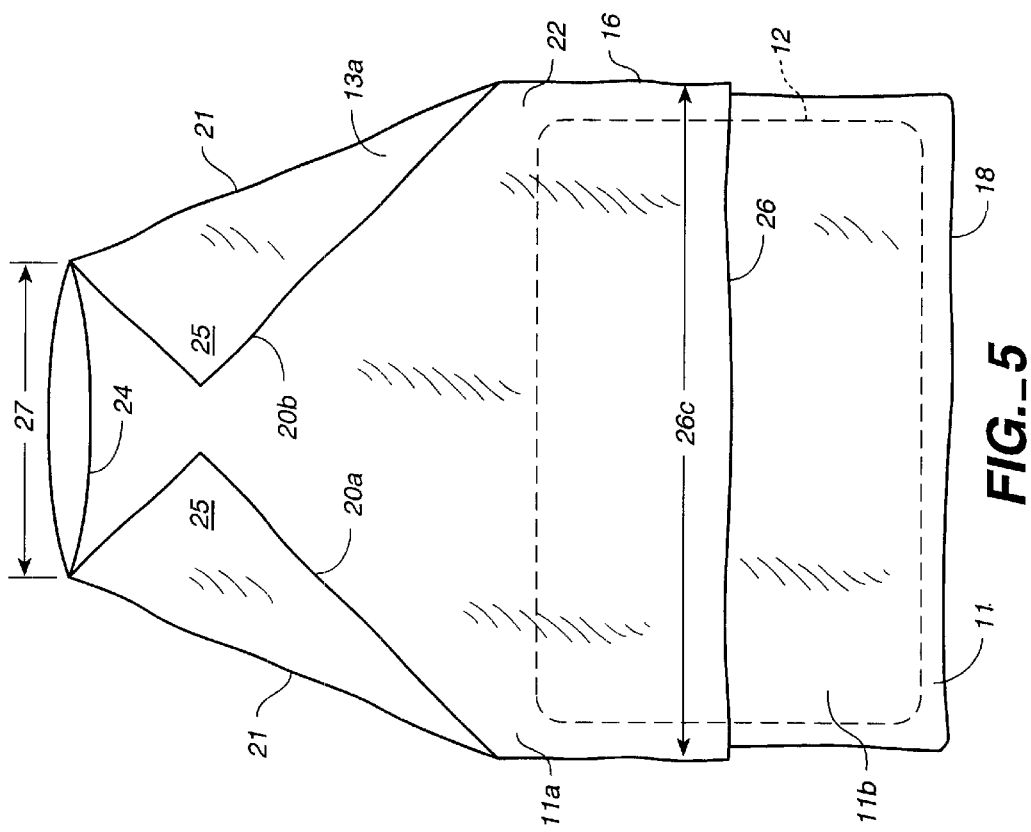
FIG._5

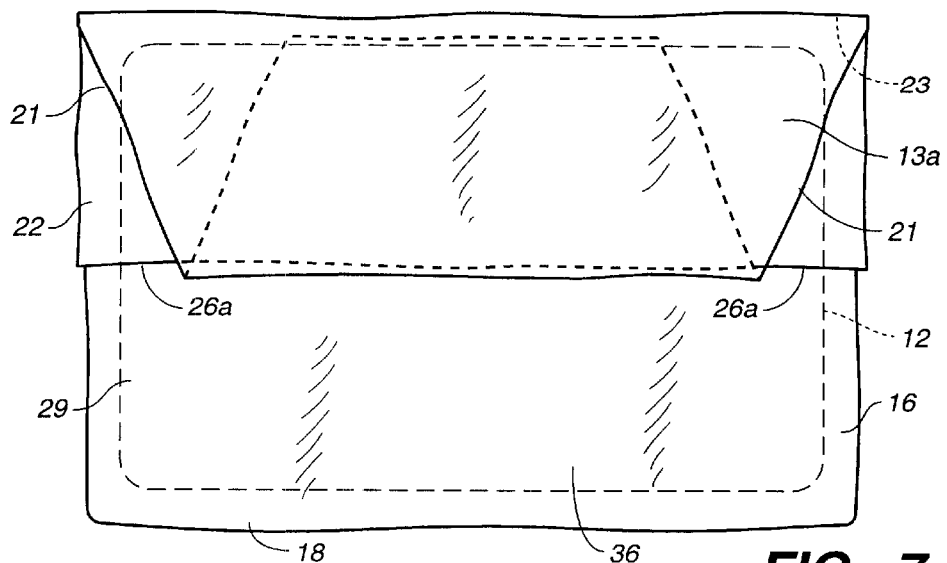
FIG._7
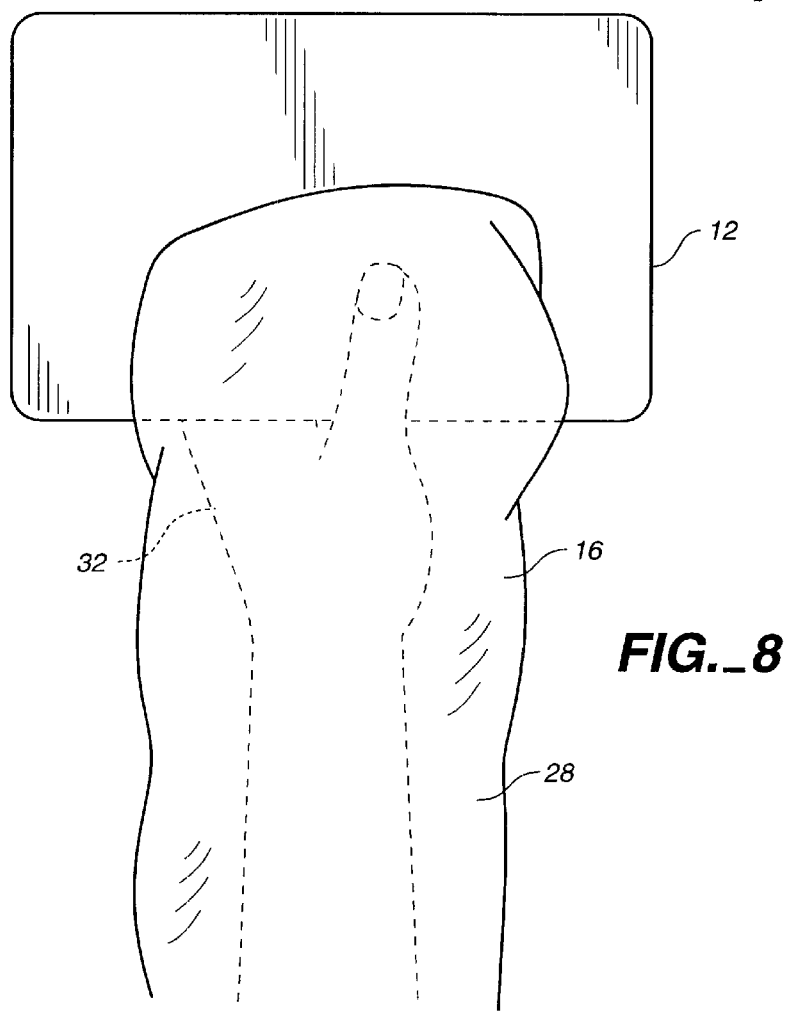
FIG._8

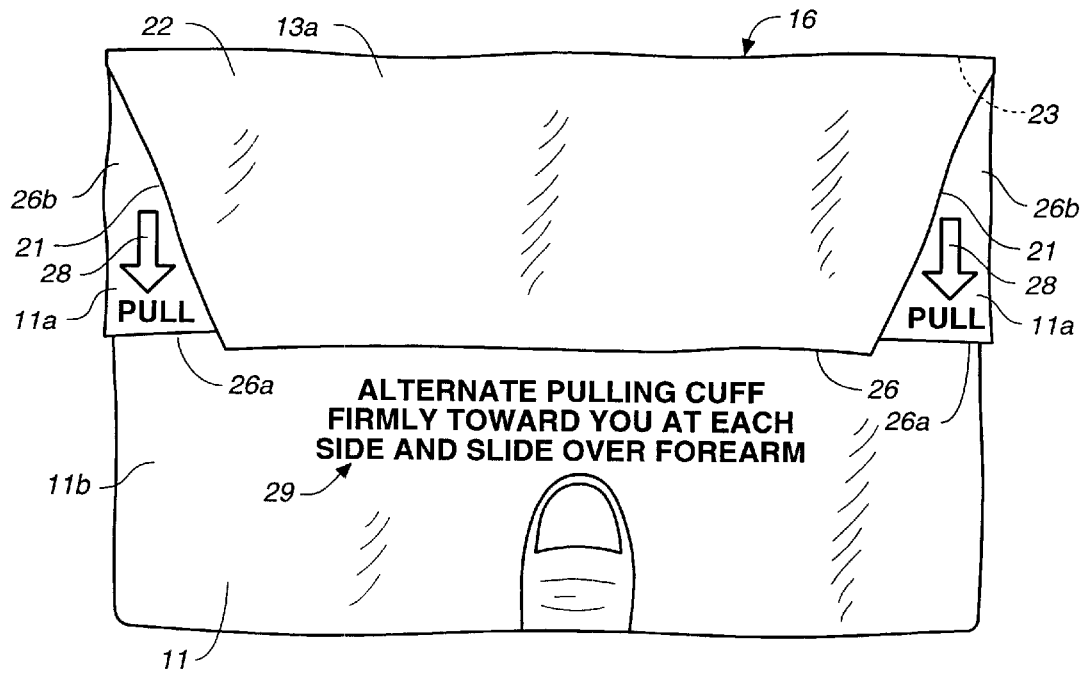
*FIG._9*
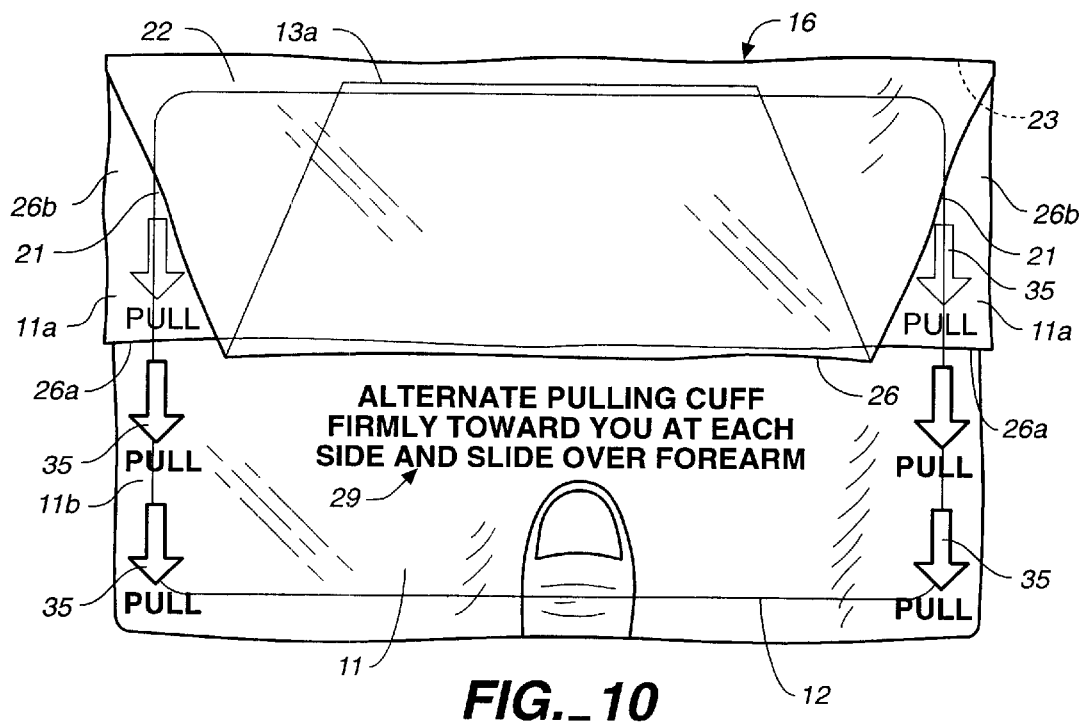
*FIG._10*

METHOD AND PACKAGING SYSTEM FOR PACKAGING A STERILIZED ITEM

BACKGROUND AND SUMMARY OF THE INVENTION

The present invention relates to a packaging system, a method for packaging a sterilizable item for aseptic presentation onto a sterile field, and a packaging element having instructional information printed thereon.

In my U.S. Pat. No. 5,638,661, I teach a method and packaging system for packaging a sterilizable item (including its container) in which a sterilizable item is placed into a flexible elongate tubular member (pouch), which tubular member is sized relative to the item being wrapped. After the tubular member is folded and secured as taught, the sterilizable item is sterilized. The packaging system can be opened and the item dispensed onto a sterile field in a manner that prevents the inadvertent contamination of the sterilized item.

The method and packaging system for packaging a sterilizable item of my U.S. Pat. No. 5,638,661 requires that the vertical orientation of the sterilizable item be reversed (turned over) as part of the packaging and unpackaging process. For many sterilizable items, this does not pose any problem, but for some sterilizable items, it is required that the vertical orientation not be reversed during or between packaging and unpackaging. That is, the item has an "up" side that must be maintained "up" at all times prior to use.

Accordingly, it is an object of the present invention to provide a method and packaging system for packaging a sterilizable item (including its container, if it has one) wherein the sterilizable item can be packaged, sterilized and unpackaged without inverting its orientation (turning it over). In achieving this objective, the present invention continues to possess all of the advantages of the invention disclosed in my prior U.S. Pat. No. 5,638,661.

Another object of the present invention is to provide a packaging element which has information printed thereon which is exposed after the packaging element is used according to the inventive packaging system and method.

The foregoing and other objectives, features and advantages of the invention will be more readily understood upon consideration of the following detailed description of the invention taken in conjunction with the accompanying drawings.

BRIEF DESCRIPTION OF THE DRAWINGS

FIG. 1 is a representation of an exemplary packaging system for a sterilizable item embodying the present invention.

FIG. 2 is a representation of an inner packaging element for the packaging system shown in FIG. 1.

FIGS. 3–7 illustrate the placement of a sterilizable item into the inner packaging element shown in FIG. 2.

FIG. 8 is a representation illustrating the aseptic presentation of the item shown in FIG. 2.

FIG. 9 is a representation illustrating information printed on the packaging element for the packaging system shown in FIG. 1.

FIG. 10 is essentially the same as FIG. 9, except that the illustrated packaging element is made of transparent polyethylene material.

DETAILED DESCRIPTION OF THE PREFERRED EMBODIMENTS

Referring now to an exemplary first embodiment illustrated in FIGS. 1–7, a packaging system 10 (FIG. 1) for a sterilizable item 12 includes an outer packaging element 14 surrounding an inner packaging element 16. The inner packaging element 16 is a sterilizable flexible pouch having a closed end 18 and an open end 19 (FIG. 3) and, in a preferred embodiment, is made by attaching a front panel 11 having an inside surface 11a and an outside surface 11b to a back panel 13 having an inside surface 13a and an outside surface 13b with at least one side seam and a bottom seam. Thus, the pouch 16 has a closed end 18, an open end 19, inside surfaces 11a and 13a, and outside surfaces 11b and 13b. The pouch 16 may be made from a reusable fabric, such as a woven fabric, or from a disposable, single-use material, such as a nonwoven fabric or a polymeric film.

Thus the packaging element 16 of the invention is formed by a front panel 11 having an inside surface 11a and an outside surface 11b, a back panel 13 having an inside surface 13a and an outside surface 13b attached to the front panel, with the inside surfaces of the front and back panels in facing relationship to form pouch 16 having a closed end 18, two sides and an open end 19 wherein the pouch is closed along at least one side.

The item 12 is placed into the pouch 16 (FIG. 4) so that the item contacts a portion of inside surfaces 11a and 13a at or near the closed end 18. The pouch 16 is sized in proportion to the particular item 12 to be enclosed. In general, the circumference of the open end of the pouch is preferably about 10–15% larger than the circumference of the item as measured when the item is oriented so that the widest part 12a of the item 12 corresponds with the width 16a of the pouch 16. Typically, the length of the pouch 16 is approximately 3.5 times the height 16b of item 12. For some items, however, that ratio will be different. In all cases, the length 16b of pouch 16 must be sufficient to enclose the hand, wrist and all or part of the forearm of a person unwrapping the item for presentation into a sterile field.

A border portion 22 (cuff is formed on the pouch 16 so that a first edge 24 of the border portion defines opening 20, which opening terminates in corners 20a and 20b. A second opposing edge 26 of border portion 22 terminates in corners 22a and 22b and is spaced apart from the first edge 24 by a width 30 of the border portion. The border portion 22 is preferably formed on the pouch 16 by folding over a circumferential cuff so that a first portion of the outside surfaces 11b and 13b of the pouch 16 contact a second portion of the outside surfaces 11b and 13b. A portion of the inside surfaces 11a and 13a of the pouch 16 are thus exposed and define the width 30 of the border portion 22 (FIG. 4).

The width of the opening 20 in the pouch 16 (FIG. 4) is reduced by approximately 50 to 80 percent to the reduced edge 27 by folding the corners 20a and 20b inward along fold lines 21 onto the border portion 22 (FIG. 5). A reduced edge 27 of at least approximately 20 percent of the length 26c of second edge 26 (or of the original width of opening 20) is required to achieve a secure lock by tucking the reduced edge 27 of the border portion 22 under the second edge 26 of the border portion 22 between the border portion 22 and the outside surface 11b of the pouch 16. When the edge 27 is reduced to zero (e.g., edge 24 folded to a point), a secure lock will not be formed by tucking edge 24 under second edge 26.

A fold line 23 (FIG. 6) is formed in the border portion 22 and the pouch panels 11 and 13 above the item 12, preferably in a manner that permits at least a portion of the inside surface 11a of front panel 11 to be in contact with at least a portion of the inside surface 13a of back panel 13, so that the reduced edge 27 of the border portion is proximate the outside surface 11b of the front panel 11. The reduced edge 27 of the border portion 22 is then placed under the second edge 26 of the border portion between the border portion and the outside surface 11b of the front panel 11 (FIG. 7).

Typically the width 30 of the border portion 22 (FIG. 4) is sufficient both to locate the second unattached edge 26 of the border portion 22 proximate the middle third of the item 12 in the pouch 16, and to permit between one-third and one-fourth of the height 30 of the border portion 22 to be tucked under the second edge 26. The size and shape of item 12 to be wrapped by element 16 dictate where the unattached edge 26 is located. In some cases, it will be in the upper or lower third of the item 12. The fraction of the border portion 22 that is tucked under the unattached edge 26 can also vary from the typical one-third to one-fourth ratio.

When the reduced edge 27 of the border portion 22 has been secured under the second edge 26 on the front panel 11 of the pouch 16, portions 26a of the second edge 26 proximate the corners 22a and 22b remain accessible for grasping without turning over the item 12. Tape may be applied to the front panel 11, if desired, to tape the border portion 22 to the pouch 16 to form a tamper-proof seal. The item 12 in the sealed pouch 16 may be sterilized without additional packaging.

The packaging system 10 is completed by placing the inner packaging element—pouch 16—enclosing the item 12, into the outer packaging element 14. The outer packaging element 14 is a sterilizable container, such as a sealable two-piece, peel-apart pouch, or a CSR cover. The packaging system 10 is sterilized by any convenient method suitable for the item and the materials used in the packaging system. After sterilization, as long as the outer packaging element 14 remains unopened and undamaged, the inner packaging element—pouch 16—and the item 12 remain sterile and ready to use.

The packaging system 10 is readily opened for aseptic presentation of the sterile item 12. The non-scrubbed attendant opens the outer packaging element 14, for example, by peeling apart the two sections of the sealed pouch (FIG. 1) and removing the inner packaging element—pouch 16— (FIG. 2). The attendant holds the inner packaging element 16 in one hand 32 at the closed end 18 with its front panel 11 and the portion 26a of the edge 26 accessible for grasping facing the attendant. With a second hand 34, the attendant grasps one of the edge portion 26a of the border portion 22 at one side of the item 12. The attendant pulls on the edge portion 26a of the border portion 22 at alternate sides of the item 12 until the first edge 24 of the border portion 22 is released from its tucked-in position under the second edge 26. The attendant continues to pull on the edge portion 26a until the pouch 16 has been turned inside out to expose generally the entire inside surfaces 11a and 13a, while, in the process, covering the attendant's hand 32 and forearm with the outside surfaces of the pouch 16 (FIG. 7). With hand 32 and forearm thus covered and protected, the non-scrubbed attendant may aseptically place the item 12 directly onto the sterile surgical field, eliminating the need for a scrubbed assistant.

At no step in the process of packaging, sterilizing, unpackaging or presenting the sterilized item into the sterile field is it necessary to invert the item being sterilized.

Importantly, the possibility of inadvertent contamination of the item and the sterile field is eliminated. Thus, one would expect a reduction in the incidence of post-operative infection when using the packaging system of the present invention in the operating room and a concomitant reduction in cost.

Referring to FIG. 9, the folding process of the present invention for a pouch 16 of opaque material not only leaves exposed portions 26a of second edge 26 for grasping to initiate the unpackaging process, but also exposes portions of the inside surface 11a of front panel 11 at areas 26b proximate second edge 26 at corners 22a and 22b and above edge portions 26a. Areas 26b being exposed (visible) when the item 12 to be sterilized is in its required vertical orientation ("up") provides the preferred location on which to print instructional information 28 in the form of words and/or symbols. Precisely where the edges 26a need to be grasped, instructions for doing so appear. Moreover, the package can be unwrapped while maintaining proper vertical orientation and achieves the other important benefits of the invention. In the prior art, it is necessary to turn the package over after completing the folding process to find the location and instructions for initiating the unwrapping process. Additional instructional information 29 (including the representation of a thumb where the users thumb should be placed) is printed on surface 11b near the bottom of panel 11.

"Printed" as used herein refers to any manner of creating visibly perceptible information on the inside or outside surfaces of front panel 11 or back panel 13.

Instructional information 28 relating to use of the invention is advantageously printed on the inside surface 11a of the front panel 11 after the border portion 22 is formed Referring to FIG. 10, a pouch 16 is formed of a clear material, such as polyethylene, which is most advantageously manufactured by a process that does not readily permit the border portion 22 to be formed prior to printing. Thus, printed "PULL" instructions 35 and instructional information 29 appear on the outside pouch surface 11b only. Because the pouch is made of transparent material, the "PULL" instructions 35 adjacent the edges 26 that underlay the border portion 22 can be seen. By printing the "PULL" instructions 35 all along the edges of panel 11 on surface 11b, there will be a "PULL" instruction adjacent each pull edge 26a, regardless of the location of the unattached edge 26 on panel 11. As with the opaque woven material, the instructional information 29 (including thumb locator) is printed near the bottom of panel 11 on surface 11b.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A packaging element for containing an item to be sterilized, comprising in combination:

a front panel having an inside surface and an outside surface;

a back panel having an inside surface and an outside surface attached to said front panel, with the inside surfaces of said front and back panels in facing relationship to form a pouch having a bottom, two sides and a top wherein said pouch is closed along its bottom and at least one side and open at its top;

instructional information printed onto the inside surface of said front panel at locations thereon which are exposed when said pouch is folded as follows:

(a) form a border portion which surrounds and overlays the outside surfaces of said front and back panels, a first edge of said border portion defining an opening in said pouch and having a width between two spaced-apart first edge corners and a second opposing edge of the border portion having a width between two second edge corners and being spaced apart from the first edge by a width of the border portion;

(b) reduce the size of the first edge by between approximately 50 to 80 percent by folding the first edge corners inward onto the border portion;

(c) fold the border portion and pouch-forming front and back panels over the first edge corners toward said front panel so that the reduced first edge extends beyond the second edge; and (d) tuck the reduced first edge of the border portion under the second edge of the border portion between the border portion and the outside surface of said front panel.

2. The packaging element of claim 1 wherein said pouch is closed on both sides.

3. The packaging element of claim 1 wherein the instructional information is printed proximate the second edge of the border portion.

4. The packaging element of claim 3 wherein additional instructional information is printed on the outside surface of said front panel adjacent the bottom of said pouch.

5. The packaging element of claim 4 wherein the instructional information printed on the inside surface of said back panel appears between the location where the border portion and pouch-forming front and back panels are folded over the first edge corners toward said front panel and the second edge of the border portion.

6. A packaging element for containing an item to be sterilized, comprising in combination:

a front panel of transparent material having an inside surface and an outside surface;

a back panel of transparent material having an inside surface and an outside surface attached to said front panel with the inside surfaces of said front and back panels in facing relationship to form a pouch having a bottom, two sides and a top wherein said pouch is closed along its bottom and at least one side and open at its top;

instructional information printed onto the outside surface of said front panel along the sides of said pouch so that when said pouch is folded as follows:

(a) form a border portion which surrounds and overlays the outside surfaces of said front and back panels, a first edge of said border portion defining an opening in said pouch and having a width between two spaced-apart first edge corners and a second opposing edge of the border portion having a width between two second edge corners and being spaced apart from the first edge by a width of the border portion;

(b) reduce the size of the first edge by between approximately 50 to 80 percent by folding the first edge corners inward onto the border portion;

(c) fold the border portion and pouch-forming front and back panels over the first edge corners toward said front panel so that the reduced first edge extends between the second edge; and (d) tuck the reduced first edge of the border portion under the second edge of the border portion between the border portion and the outside surface of said front panel exposing portions of the second opposing edge of the border portion and areas of said border portion immediately above said exposed second opposing edge portions;

the instructional information appears adjacent the exposed portions of the second opposing edge of the border portion and under said areas of said border portion immediately above said exposed second opposing edge portions.

7. The packaging element of claim 6 wherein said printed instructional information appears near the bottom of said front panel of said pouch.

8. A packaging element for containing an item to be sterilized manufactured according to the following steps:

a front panel of sterilizable material having an inside surface and an outside surface is attached to a back panel of sterilizable material having an inside surface and an outside surface with the inside surfaces of said front and back panels in facing relationship to form a pouch having a bottom, two sides and a top wherein said pouch is closed along its bottom and at least one side and open at its top;

form a border portion which surrounds and overlays the outside surfaces of said front and back panels and exposes a portion of the inside surface of said front panel, a first edge of said border portion defining an opening in said pouch and a second opposing edge of the border portion being spaced apart from the first edge by a width of the border portion;

printing instructional information onto the exposed inside surface of said front panel forming said border portion.

\* \* \* \* \*